US00PP13139P2

(12) United States Plant Patent
Kuijf

(10) Patent No.: US PP13,139 P2
(45) Date of Patent: Oct. 29, 2002

(54) *CAMPSIS×TAGLIABUANA* PLANT NAMED 'KUDIAN'

(75) Inventor: Hendricus Jacobus Maria Kuijf, Uithoorn-Amstelhoek (NL)

(73) Assignee: Pride of Place Plants, Inc., British Columbia (CA)

( * ) Notice: Subject to any disclaimer, the term of this patent is extended or adjusted under 35 U.S.C. 154(b) by 0 days.

(21) Appl. No.: 09/115,663

(22) Filed: Jul. 15, 1998

(51) Int. Cl.[7] ..... A01H 5/00
(52) U.S. Cl. ..... Plt./226
(58) Field of Search ..... Plt./226

(56) References Cited

U.S. PATENT DOCUMENTS

PP4,119 P * 10/1977 Flemer ..... Plt./226
PP12,245 P2 * 12/2001 Wakaiki ..... Plt./226

OTHER PUBLICATIONS

UPOV ROM GTITM Computer Database, GTI JOUVE Retrieval Software, citation for 'Kudian'.*

* cited by examiner

*Primary Examiner*—Bruce R. Campell
*Assistant Examiner*—Wendy C Baker
(74) *Attorney, Agent, or Firm*—Christie, Parker & Hale, LLP

(57) ABSTRACT

A new and distinct plant producing trumpet-shaped flowers of a good quality and attractive coloration on a twining, vine-like plant.

1 Drawing Sheet

BOTANICAL CLASSIFICATION

*Campsis×tagliabuana* (*C. grandiflora×C. radicans*).

BACKGROUND OF THE INVENTION

The present invention relates to a new and distinct variety of Campsis plant which is a cross of an unnamed *Campsis grandiflora* as seed parent and an unnamed *Campsis radicans* as pollen parent. The varietal denomination of the new variety is 'Kudian'.

The first act of asexual reproduction of 'Kudian' was in Uithoorn, The Netherlands, by grafting onto *Campsis radicans*. Asexual reproduction by graftings through successive generations in Uithoorn, The Netherlands, has demonstrated that the combination of characteristics as herein disclosed for 'Kudian' are firmly fixed and retained through successive generations.

Seeds from a cross of *Campsis grandiflora×Campsis radicans* were harvested in 1984 and were planted in the soil in autumn 1984.

In January 1987 the seedlings (in total 10 plants) were grafted on *Campsis radicans* as the rootstock. Grafting is desired to get fast flowering. In summer 1987 all the plants flowered. One of them (identified as 'KU 52', now known as 'Kudian') was different than the other seedlings in the following characteristics:

1. Very early flowers
2. Many flowers on one plant
3. Dark green leaves
4. Different orange color of the flowers From 1988 until 1994 'Kudian' was propagated through grafting. The variety was found to be 100% stable. During this period it also appeared that all plants flowered more profusely as compared with the existing variety *Campsis×taglibuana* 'Mdm Galen'. If, for instance, 100 plants of *Campsis×taglibuana* 'Mdm Galen' are planted, only about 70% will flower. If 100 plants of 'Kudian' are planted, they all will flower.

Further growing of plants of 'Kudian' demonstrated the homogeneity and flowering characteristics thereof.

SUMMARY OF THE INVENTION

The new variety flowers heavily as a young plant and produces large flowers of attractive color.

COMPARISION WITH PARENTS

The new variety produces larger flowers than either parent and exhibits different flower color. It further differs from its parents in flowering very early, producing dark green foliage and having a different orange flower color.

DESCRIPTION OF ILLUSTRATION

The new variety is illustrated in the accompanying illustration, which shows typical flower and growth characteristics, with colors being as nearly true as is possible for illustrations of this type.

DETAILED DESCRIPTION OF THE NEW VARIETY

The following is a detailed description of a three year-old plant of the new cultivar as observed in a greenhouse in The Netherlands. Color designations indicated are in accordance with The Royal Horticultural Society Colour Chart (2001) by color plate designations.

'Kudian' has not been observed under all possible environmental conditions. Phenotypic expression may vary with variations in environment such as temperature, light intensity, day length and growing and cultural conditions.

DESCRIPTION

'Kudian' exhibits a climbing habit of about 4 m to 4.6 m high. Leaves are pinnate, dull to shiny dark green. Flowers are often arranged in large, pendulous racemes, trumpet-shaped, having a corolla 5–6 cm across. The color of the outside of the flower is yellowish-orange, while the interior of the flower is orange-red. Flowering occurs in July to September in Uithoorn, The Netherlands.

'Kudian' is a very attractive, abundantly flowering plant. When grown in a pot in a greenhouse,the flowers are more of an orange color, with orange red throats and red stripes running lengthways. Also, as a flowering plant, 'Kudian' does not grow as tall as other cultivars, making it an attractive pot plant for the consumer. Grown against a wall, this trumpet-flower climber will start flowering quite well within a few years. It is propagated by grafting and is sufficiently hardy to survive a normal winter.

Plant:

*Form.*—Vine.

*Growth.*—Twining vine.

*Height attained.*—About 458 cm.

*Shoots.*—Produces about 3 to 5 shoots, about 27 cm apart.

*Foliage.*—Pubescent, internodal spacing about 20 cm, growth about 50–60 cm per season. Leaf shape: Pinnate, with about 7 to 9 leaflets per leaf. Leaflet shape: Lanceolate-elliptic; base attenuate, apex apiculate. Leaf length: Average — 34 cm (varying from 25 to 40 cm). Leaf width: Average — 13 cm. Leaflet length: Average — 8 cm. Leaflet width: Average — 4 cm. Color: Upper side: dark green, near 139A; Underside: dull, dark green, near 138B. Texture: Upper side smooth. Underside smooth. Edge: Serrated. Serration: Irregular. Petioles: Green, near 139A.

*Wood.*—Branching Characteristics (2-year old plant): An average of 3 main stems grow from the base of the plant, with an average of 3 lateral branches per main stem; average length of a lateral shoot is 35 cm. Bark Color: Greyish-brown, near 199A to 199B. New Shoots: Color: Green, near 138B. Bark: Smooth.

*Flowers.*—Quantity (per raceme): Average — 22. Type: Single. Aspect: Outward to slightly upright (average angle: 40°). Shape: Tubular-funnelform. Size: Length about 9 cm, width about 6 cm. Petals Quantity: 5. Shape: Elliptic. Color: Inside near 30D to near 39A; outside near 26A. Veins: Orange red, near 34B to 34C. Peduncle: Present; length about 2.5 cm; pubescence is present; color green, near 141B. Pedicel: Green to yellowish green, near 143A to 144A. Lastingness: About 7–10 days on plant. Fragrance: No fragrance. Buds: Color: Orange, near 26B to 26C. Length: Average—5.5 cm (approximately 3 days before opening). Diameter: About 1.4 cm (approximately 3 days before opening). Shape: Oblong to oblanceolate.

*Reproductive parts.*—Stamen Quantity: About 5. Length: About 3.5 cm. Color: Green-yellow. Anthers Quantity: 2. Length: About 3.5 cm. Color: Pale yellow to light orange-yellow. Pistil Style: Pale yellow to light orange-yellow. Stigma: Light yellow. Pollen: Present, light yellow. Fruit: Color near 200D, bean-shaped.

*Winter hardiness.*—Completely winter hardy to Zone 5.

*Resistance to disease.*—No unusual susceptibility to disease noted.

I claim:

1. A new Campsis plant substantially as herein shown and described.

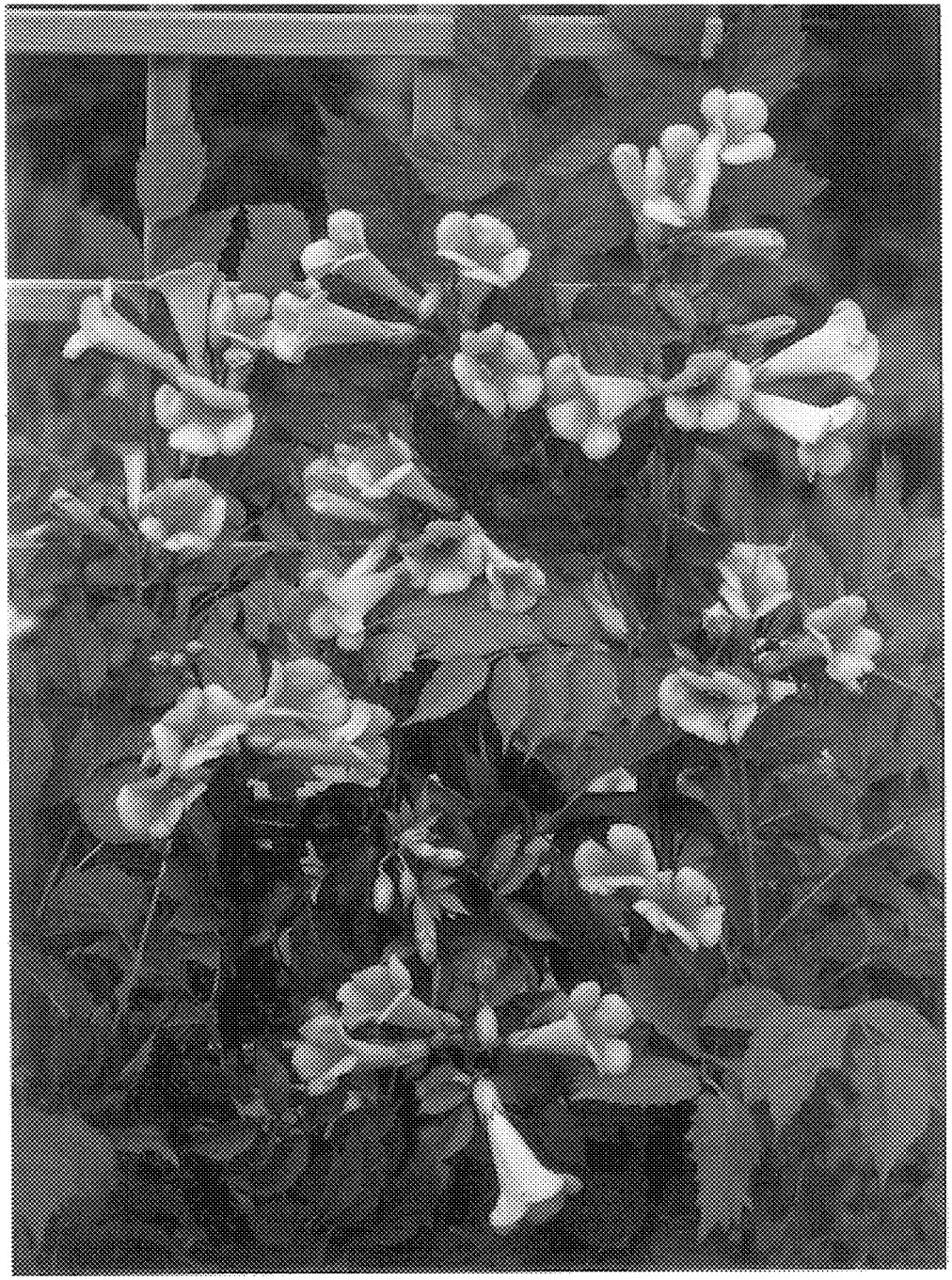

* * * * *